(12) United States Patent  (10) Patent No.: US 6,319,216 B1
Coligado  (45) Date of Patent: Nov. 20, 2001

(54) PELVIC BRACING SYSTEM

(75) Inventor: Joseph Coligado, Melrose Park, IL (US)

(73) Assignee: Hipbolt Orthopedic Systems, Inc., Melrose Park, IL (US)

( * ) Notice: Subject to any disclaimer, the term of this patent is extended or adjusted under 35 U.S.C. 154(b) by 0 days.

(21) Appl. No.: 09/489,599

(22) Filed: Jan. 20, 2000

Related U.S. Application Data

(60) Provisional application No. 60/116,645, filed on Jan. 21, 1999.

(51) Int. Cl.[7] ........................................................ A61F 5/00
(52) U.S. Cl. ............................. 602/5; 602/19; 602/24
(58) Field of Search ............................... 128/845, 846, 128/869, 876, 95.1, 96.1; 602/5, 16, 19, 23, 24

(56) References Cited

U.S. PATENT DOCUMENTS

| | | | |
|---|---|---|---|
| 5,363,863 | * 11/1994 | Lelli | 602/19 |
| 5,690,609 | * 11/1997 | Helenze | 602/19 |
| 5,830,168 | 11/1998 | Finnell et al. | 602/24 |
| 5,911,697 | * 6/1999 | Biedermann | 602/19 |
| 6,015,395 | * 1/2000 | Kautzky | 602/19 |
| 6,213,558 | * 4/2001 | Axelson | 297/464 |

* cited by examiner

Primary Examiner—Michael A. Brown
(74) Attorney, Agent, or Firm—Pauley Petersen Kinne & Fejer

(57) ABSTRACT

A pelvic bracing system having a first hip plate connected with respect to a second hip plate. The first hip plate and the second hip plate are laterally and/or rotationally adjustable with respect to a posterior panel to properly fit a posterior pelvic region of a patient. The first hip plate and the second hip plate are laterally and/or rotationally adjustable with respect to an anterior panel to properly fit an anterior pelvic region of the patient.

20 Claims, 6 Drawing Sheets

PELVIC BRACING SYSTEM

CROSS REFERENCE TO RELATED APPLICATION

This application claims the benefit of U.S. Provisional Application No. 60/116,645, filed Jan. 21, 1999, the disclosure of which earlier application is hereby incorporated by reference herein and made a part hereof, including but not limited to those portions which specifically appear hereinafter.

BACKGROUND OF THE INVENTION

1. Field of the Invention

This invention relates to a pelvic bracing system for use in post-operative rehabilitation and/or to combat the effects of chronic disease. More specifically, this invention relates to a pelvic bracing system having a posterior panel and an anterior panel for hip and waist adjustments, as well as for rotational and/or twisting stability, to provide a more comfortable and uniform fit for a patient.

2. Description of Related Art

Conventional pelvic braces generally have an open "C" configuration, with no circumferential support in the anterior portion of the pelvic brace. For example, many conventional pelvic braces have a first hip brace connected to a second hip brace with a posterior strap. Such conventional pelvic braces demonstrate a considerable amount of twisting and/or rotation of the first hip brace with respect to the second hip brace resulting in discomfort for the patient and loss of control between the pelvic brace and a thigh cuff constraining the joint.

Further, conventional pelvic braces generally are compatible with only one type or brand of orthopedic joint which connects the pelvic brace with the thigh cuff to support the patient's hip. Thus, conventional pelvic braces are not compatible with many of the existing orthopedic joints.

Therefore, there exists a need for a pelvic bracing system which provides sufficient circumferential and rotational support to control the movement of the thigh cuff thereby controlling the range of motion of the patient's hip joint.

It is also apparent that there exists a need for a pelvic bracing system which is adjustable to a patient's pelvic region to provide a comfortable fit.

It is further apparent that there exists a need for a pelvic bracing system that is universally compatible with existing orthopedic joints.

SUMMARY OF THE INVENTION

It is one object of this invention to provide a pelvic bracing system which provides circumferential and rotational support that is laterally and rotationally adjustable to properly fit a pelvic region and control the range of motion of the patient's hip joint via the metal joint connection with the thigh cuff.

It is another object of this invention to provide an adjustable pelvic bracing system that is universally compatible with existing orthopedic joints.

The above and other objects of this invention are accomplished with a pelvic bracing system having a first hip plate and a second hip plate pivotally connected with respect to one another. The first hip plate has a posterior portion or side with a first attachment aperture and a first adjustment slot or aperture configured in an arcuate or crescent shape. Similarly, the second hip plate has a second attachment aperture and a second adjustment slot or aperture on a posterior portion or side of the second hip plate configured in an arcuate or crescent shape.

The pelvic bracing system has a posterior panel with a first end portion positioned with respect to the posterior portion of the first hip plate and a second end portion positioned with respect to the posterior portion of the second hip plate. The posterior panel is connected to the posterior portions with a plurality of adjustment screws.

With the first end portion of the posterior panel connected to the first hip plate and the second end portion connected to the second hip plate, the first hip plate and second hip plate are adjustable with respect to the posterior panel, to properly fit the patient. The first hip plate and the second hip plate are adjustable laterally by sliding the hip plate along the corresponding sizing channel and rotationally by guiding an adjustment screw along an arcuate-shaped adjustment slot. After the first hip plate and the second hip plate are fitted laterally and rotationally with respect to a posterior pelvic region, the adjustment screws are tightened to secure the first hip plate and the second hip plate to the posterior panel.

An anterior portion or side of the first hip plate is connected to an anterior portion or side of the second hip plate with an anterior panel. The adjustable anterior panel comprises an inner plate and an outer plate each having a plate attachment aperture or slot and a plate adjustment slot or aperture for attachment with respect to an inner surface of the anterior portion of the first hip plate and an inner surface of the anterior portion of the second hip plate.

The plate attachment apertures are aligned with a connecting aperture and an adjustment screw is inserted through the connecting aperture and the plate attachment aperture to securely fasten or connect the inner plate to the anterior portion of the second hip plate and the outer plate to the anterior portion of the first hip plate. The plate adjustment slot is aligned with another connecting aperture and an adjustment screw is inserted through the other connecting aperture and the plate adjustment slot.

An inner surface of the outer plate and an outer surface of the inner plate each has a fastening means, for example VELCRO brand hook and loop fastener or other similar fastening means. The inner surface is adjustably fastenable to the outer surface to securely connect the anterior portion of the first hip plate to the anterior portion of the second hip plate. The anterior panel provides circumferential support that aids in the function of the pelvic bracing system to provide stability and eliminate or reduce rotational and/or twisting motion of the pelvic bracing system.

The anterior panel allows the adjustment of the pelvic bracing system laterally and/or rotationally with respect to a patient's anterior pelvic region. Anterior lateral adjustment is accomplished by adjusting the connection between the inner plate and the outer plate. Anterior rotational adjustment is accomplished by means similar to the rotational adjustment of the posterior panel.

The bracing system preferably further includes a belt positioned over the anterior panel to connect the first hip plate with respect to the second hip plate. The belt has a removable first strap with a removable female buckle portion that is mateable with a second strap having a removable male buckle portion to connect the first hip plate with the second hip plate. The first strap can be disconnected from a chaff and loop and the male buckle portion can be removed from the second strap. The second strap is then insertable through the chaff and loop to connect the first hip plate with the second hip plate.

A universal mounting block, having a plurality of threaded channels, is preferably mounted with respect to the first hip plate. The threaded channels are positioned to accept various corresponding articulating orthopedic joints, which are attached to a thigh cuff to add support to the pelvic bracing system.

BRIEF DESCRIPTION OF THE DRAWINGS

The above-mentioned and other features and objects of this invention will be better understood from the following detailed description taken in conjunction with the drawings wherein.

DESCRIPTION OF PREFERRED EMBODIMENTS

Figure 1:
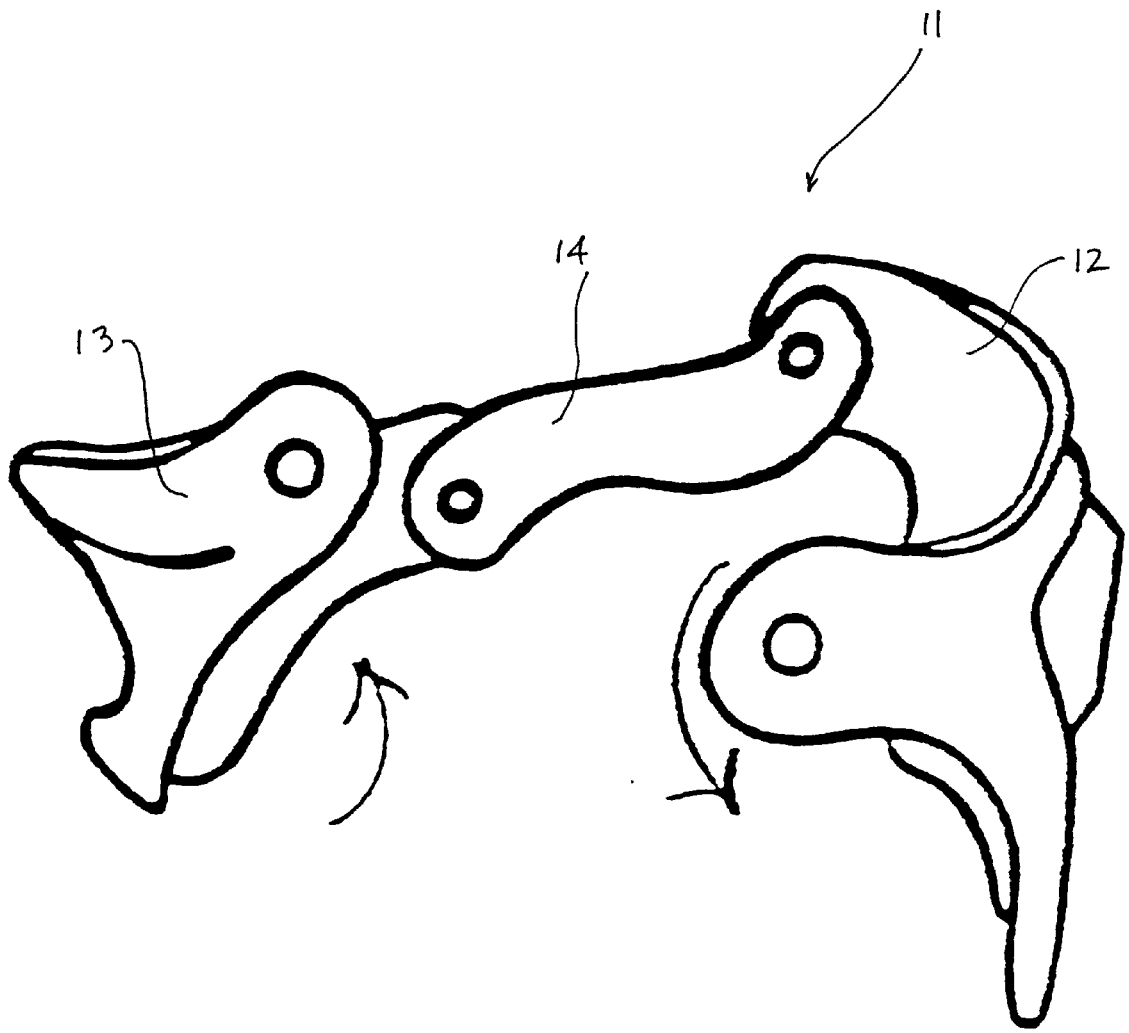
FIG. 1 is a perspective front view of a prior art hip brace without front panel stability.

As described above, conventional pelvic braces generally have an open "C" configuration, with no circumferential support in the anterior portion of the pelvic brace. For example, as shown in FIG. 1, a conventional pelvic brace 11 has a first hip brace 12 connected to a second hip brace 13 by a posterior strap 14. Conventional pelvic brace 11 demonstrates a considerable amount of twisting and/or rotation of first hip brace 12 with respect to second hip brace 13. Thus, conventional pelvic brace 11 does not fit the patient comfortably, nor does conventional pelvic brace 11 provide adequate circumferential support to prevent twisting and/or rotation of hip braces 12 and 13 with respect to one another. Additionally, hip braces 12 and 13 of conventional pelvic brace 11 are not securely adjustable to properly fit the pelvic region to provide a comfortable fit for the patient.

Conventional hip braces, as well as pelvic bracing system 15 according to this invention, typically include a thigh cuff connected to one side of the hip brace with an articulating joint. The articulating joint, referred to as a joint herein, limits the range of motion of the patient's hip joint by limiting the permissible range of motion between the hip brace and the thigh cuff.

Figure 2:
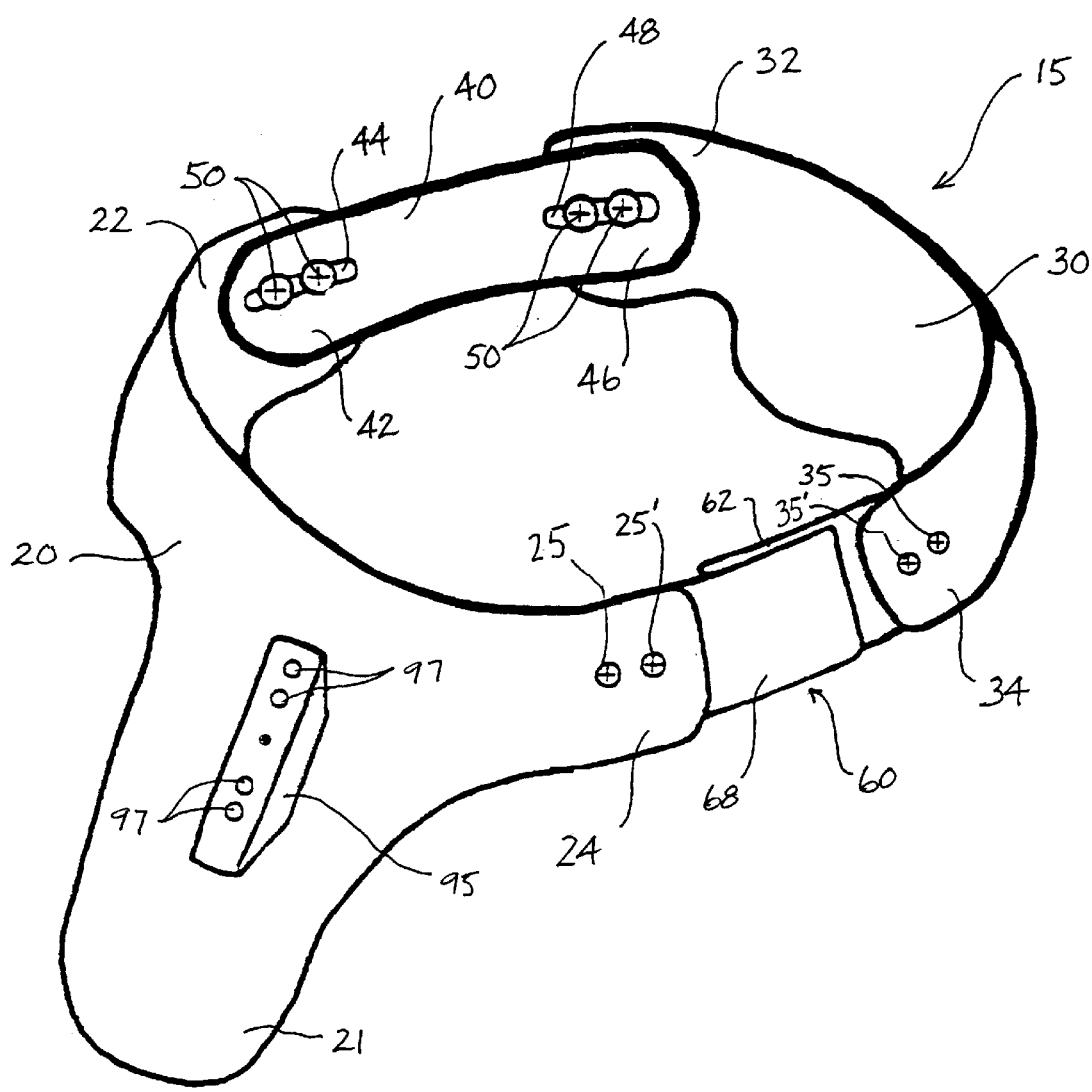
FIG. 2 is a perspective front view of a pelvic bracing system, according to one preferred embodiment of this invention.

Referring to FIG. 2, pelvic bracing system 15 comprises a first hip plate 20 and a second hip plate 30 pivotally connected with respect to one another. Preferably, first hip plate 20 and second hip plate 30 are positioned with respect to a pelvic region or area of a patient so that first hip plate 20 is positioned with respect to an injured and/or disabled right hip region and second hip plate 30 is positioned with respect to the patient's left hip region.

Figure 5:
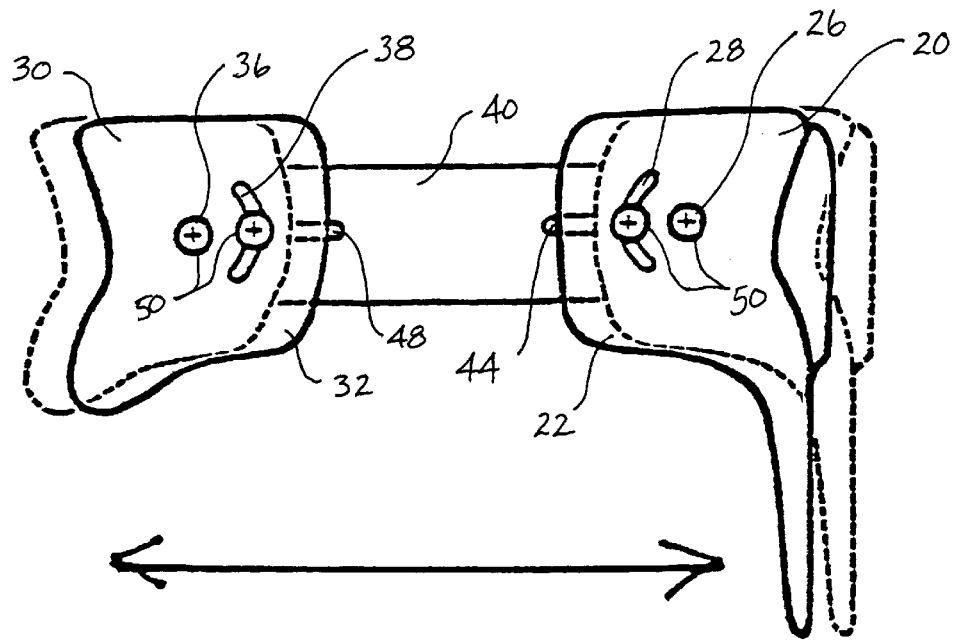
FIG. 5 is a front view of a laterally adjustable posterior panel mounted to a first hip plate and a second hip plate of a pelvic bracing system, according to one preferred embodiment of this invention.
Figure 6:
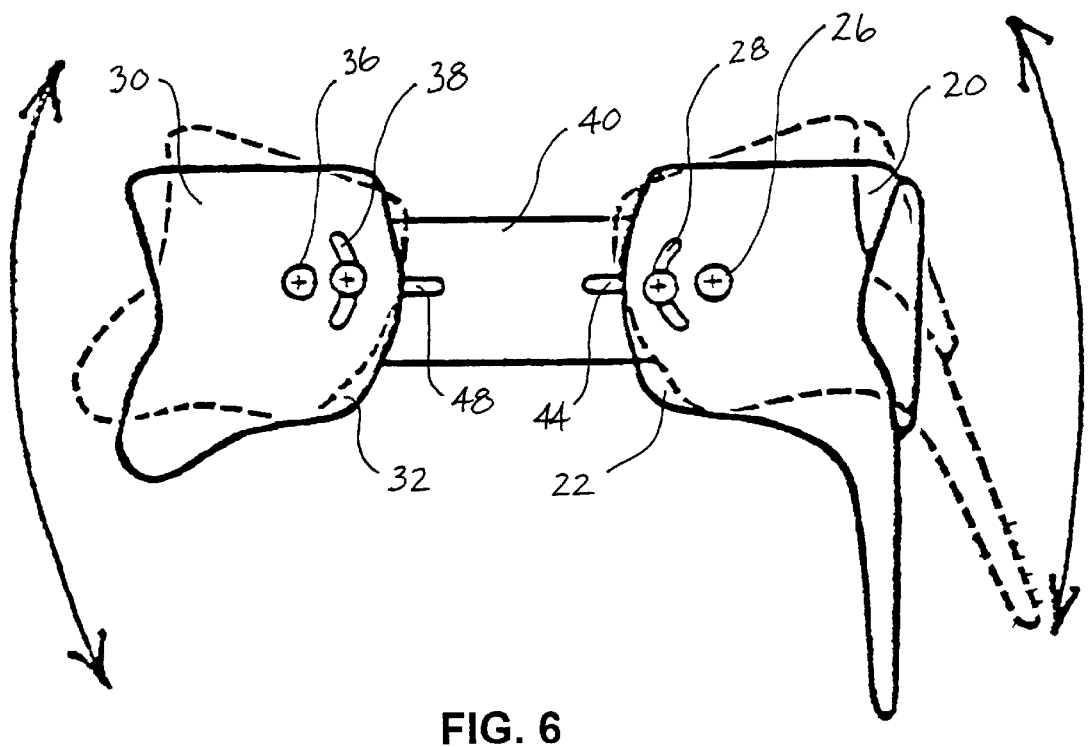
FIG. 6 is a front view of a rotationally adjustable posterior panel mounted to a first hip plate and a second hip plate of a pelvic bracing system, according to one preferred embodiment of this invention.

In one preferred embodiment of this invention, first hip plate 20 has a general shape that conforms to the right hip region. First hip plate 20 has a posterior portion or side 22 having a first attachment aperture 26 and a first adjustment slot or aperture 28. Preferably, first adjustment slot 28 is configured in an arcuate or crescent shape, as shown in FIGS. 5 and 6. First adjustment slot 28 may be configured in any suitable shape, for example a linear shape or a circular shape.

Similarly, second hip plate 30 has a general shape that conforms to the left hip region. Second hip plate 30 has a second attachment aperture 36 and a second adjustment slot or aperture 38 on a posterior portion or side 32 of second hip plate 30. Preferably, second adjustment slot 38 is configured in an arcuate or crescent shape, as shown in FIGS. 5 and 6. Like first adjustment slot 28, second adjustment slot 38 may be configured in any suitable shape.

Figure 3:
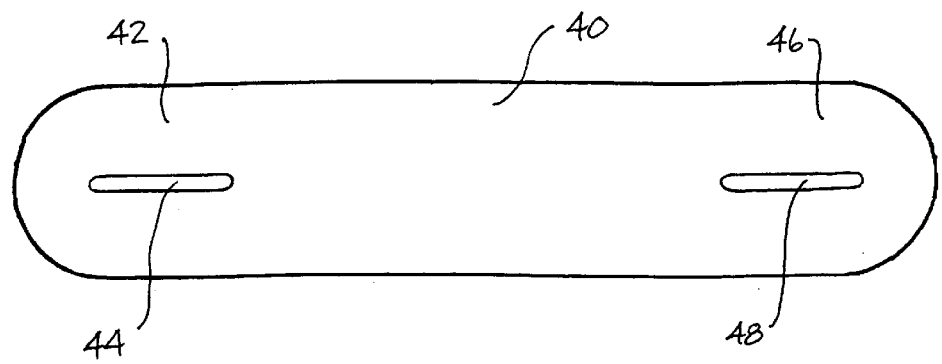
FIG. 3 is a front view of a posterior panel for a pelvic bracing system, according to one preferred embodiment of this invention.

In one preferred embodiment of this invention, pelvic bracing system 15 comprises a posterior panel 40, as shown in FIG. 3. Posterior panel 40 has a first end portion 42 positioned with respect to posterior portion 22 of first hip plate 20 and a second end portion 46 positioned with respect to posterior portion 32 of second hip plate 30. Posterior panel 40 is connected to posterior portion 22 and posterior portion 32 with a plurality of adjustment screws 50. Preferably, but not necessarily, posterior panel 40 is positioned to contact an inner surface of posterior portion 22 and an inner surface of posterior portion 32.

Posterior panel 40 allows lateral adjustment and rotational adjustment of pelvic bracing system 15 with respect to the pelvic region of the patient. Preferably, first end portion 42 comprises a first sizing channel or aperture 44 extending laterally along first end portion 42 and positioned with respect to posterior portion 22 of first hip plate 20. First sizing channel 44 is aligned with first attachment aperture 26 and first adjustment slot 28. According to one preferred embodiment of this invention, an adjustment screw 50 is inserted through first attachment aperture 26 and first sizing channel 44 and an additional adjustment screw 50 is preferably inserted through first adjustment slot 28 and first sizing channel 44 to mount or connect first end portion 42 to first hip plate 20. Preferably, adjustment screw 50 comprises a truss nut and a barrel screw, which tightens down on first hip plate 20 to secure first hip plate 20 to first end portion 42. Other suitable mounting or connecting means known to those having ordinary skill in the art may be used for mounting or connecting first end portion 42 with first hip plate 20.

Similarly, as shown in FIG. 3, second end portion 46 of posterior panel 40 comprises a second sizing channel or aperture 48 positioned with respect to posterior portion 32 of second hip plate 30 and extending laterally along second end portion 46. Second sizing channel 48 is aligned with second attachment aperture 36 and second adjustment slot 38 An adjustment screw 50 is inserted through second attachment aperture 36 and second sizing channel 48 and an additional adjustment screw 50 is inserted through second adjustment slot 38 and second sizing channel 48 to mount or connect second end portion 46 to second hip plate 30.

In one preferred embodiment of this invention, adjustment screw 50 has an enlarged head. Preferably, adjustment screw 50 is threadedly connected to a nut having an enlarged contact surface area to provide an enlarged mating surface. Preferably, but not necessarily, the mating surface has an outer diameter of about 0.5 inch to about 1.0 inch. The enlarged mating surface allows posterior panel 40 to be securely fastened to first hip plate 20 and second hip plate 30. Preferably, a bottom surface of the enlarged head of adjustment screw 50 and/or the enlarged contact surface area of the nut has a plurality of serrated projections to secure posterior panel 40 to first hip plate 20 and second hip plate 30.

Referring to FIGS. 5 and 6, with first end portion 42 connected to first hip plate 20 and second end portion 46 connected to second hip plate 30, first hip plate 20 and second hip plate 30 are adjustable with respect to posterior panel 40, to properly fit the patient. As shown in FIG. 5, first hip plate 20 is adjustable laterally by sliding first hip plate 20 laterally along first sizing channel 44. Similarly, second hip plate 30 is adjustable laterally by sliding second hip plate 30 laterally along second sizing channel 48. After first hip plate 20 and second hip plate 30 are fitted laterally with respect to a posterior pelvic region, adjustment screw 50 positioned within first attachment aperture 26 and adjustment screw 50 positioned within second attachment aperture 36 are tightened to laterally secure first hip plate 20 and second hip plate 30 with respect to posterior panel 40. Preferably, adjustment screw 50 positioned within first adjustment aperture 26 and adjustment screw 50 positioned within second adjustment aperture 36 are in a slightly loosened state so that first hip plate 20 and second hip plate can be rotationally adjusted with respect to posterior panel 40.

As shown in FIG. 6, first hip plate 20 is rotationally adjustable with respect to posterior panel 40 by guiding adjustment screw 50 along arcuate-shaped first adjustment slot 28. Adjustment screw 50 positioned in a slightly loosened state within first attachment aperture 26 acts as a pivot point for guiding adjustment screw 50 along first adjustment slot 28. Similarly, second hip plate 30 is rotationally adjustable with respect to posterior panel 40 by guiding adjustment screw 50 along arcuate-shaped second adjustment slot 38, with adjustment screw 50 positioned within second attachment aperture 36 acting as a pivot point. Corresponding adjustment screws 50 are then rotated to secure pelvic bracing system 15 rotationally with respect to the posterior pelvic region.

An anterior portion or side 24 of first hip plate 20 is connected to an anterior portion or side 34 of second hip plate 30 with an anterior panel 60, as shown in FIG. 2. Preferably, but not necessarily, anterior panel 60 is positioned with respect to an inner surface of anterior portion 24 and an inner surface of anterior portion 34.

Figure 4:
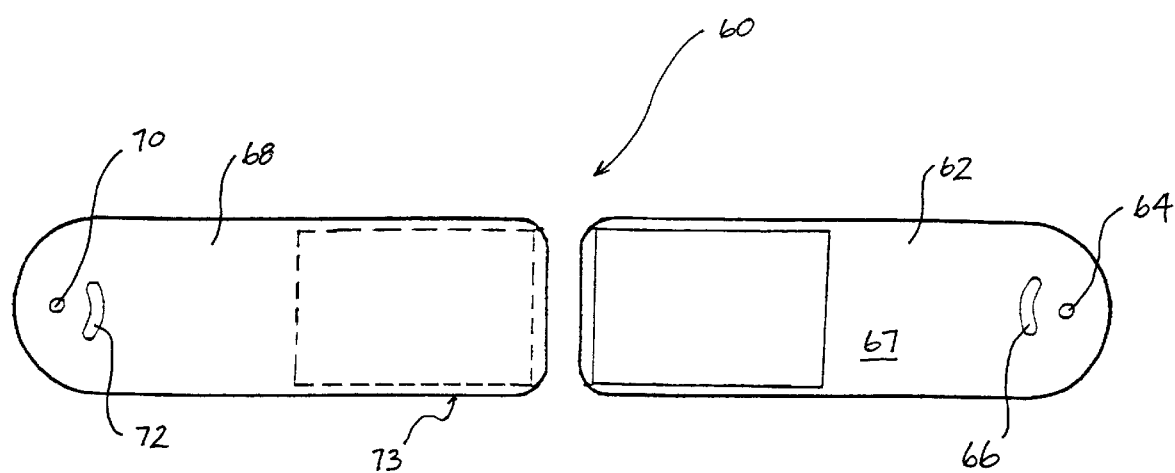
FIG. 4 is a front view of an anterior panel for a pelvic bracing system having an inner panel mateable with an outer panel, according to one preferred embodiment of this invention.

In one preferred embodiment of this invention, adjustable anterior panel 60 comprises an inner plate 62 having a first plate attachment aperture or slot 64 and a first plate adjustment aperture or slot 66 for attachment with respect to the inner surface of anterior portion 34, as shown in FIG. 4. First plate adjustment slot 66 has an arcuate or crescent shape to permit rotational adjustment of second hip plate 30 with respect to pelvic bracing system 15.

As shown in FIG, 4, first plate attachment aperture 64 is aligned with a connecting aperture 35 and adjustment screw 50 is inserted through connecting aperture 35 and first plate attachment aperture 64 to securely fasten or connect inner plate 62 to anterior portion 34. Other suitable connecting means, for example a rivet, which allows rotation of inner plate 62 about the connecting means positioned within first plate attachment aperture 64 may also be used to fasten inner plate 62 to anterior portion 34. First plate adjustment slot 66 is aligned with a connecting aperture 35' and adjustment screw 50 is inserted through connecting aperture 35' and first plate adjustment slot 66.

Referring to FIG. 2, inner plate 62 is mateable with an outer plate 68. Outer plate 68, preferably but not necessarily the same or similar to inner plate 62, comprises a second plate attachment aperture 70 and a second plate adjustment slot or aperture 72 for attachment with respect to anterior portion 24, as shown in FIG. 4. Second plate adjustment slot 72 has an arcuate or crescent shape to permit rotational adjustment of first hip plate 20 with respect to pelvic bracing system 15.

Preferably, second plate attachment aperture 70 is aligned with a connecting aperture 25 of anterior portion 24. Adjusting screw 50 or a rivet, for example, is inserted through connecting aperture 25 and second plate attachment aperture 70 to connect outer plate 68 to anterior portion 24. Second plate adjustment slot 72 is aligned with a connecting aperture 25' and an additional adjustment screw 50 is inserted through connecting aperture 25' and second plate adjustment slot 72.

At least a portion of an inner surface 73 of outer plate 68 and at least a portion of an outer surface 67 of inner plate 62 each has a fastening means, for example VELCRO brand hook and loop fastener or other fastening means known to those having ordinary skill in the art. Inner surface 73 is adjustably fastenable to outer surface 67 to securely connect anterior portion 24 with anterior portion 34 and provide proper circumferential support for the patient. Circumferential support aids in the function of pelvic bracing system 15 to provide stability and eliminate or reduce rotational and/or twisting motion of pelvic bracing system 15 relative to the patient.

Figure 7:
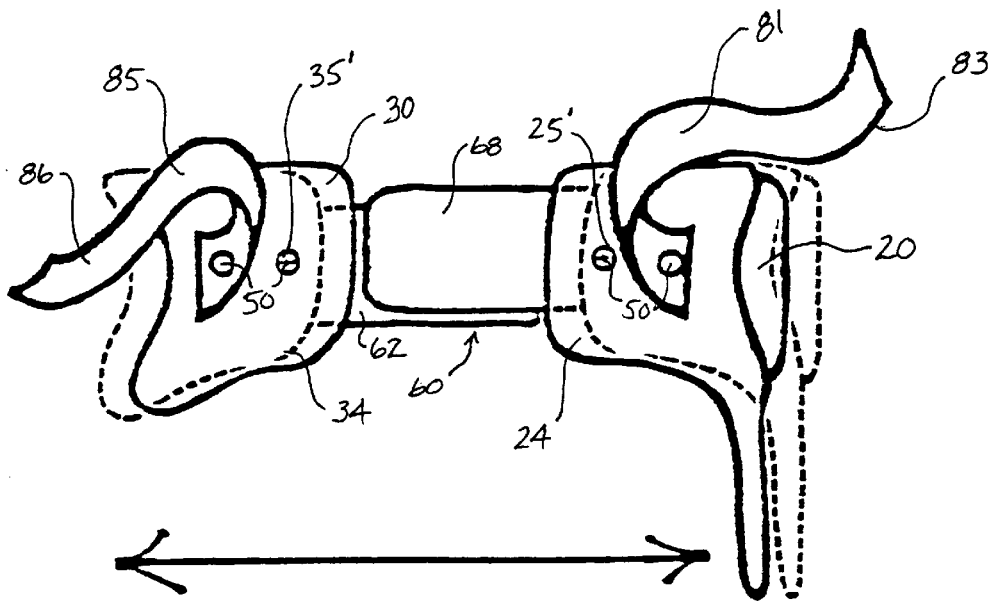
FIG. 7 is a front view of a laterally adjustable anterior panel mounted to a first hip plate and a second hip plate of a pelvic bracing system, according to one preferred embodiment of this invention.
Figure 8:
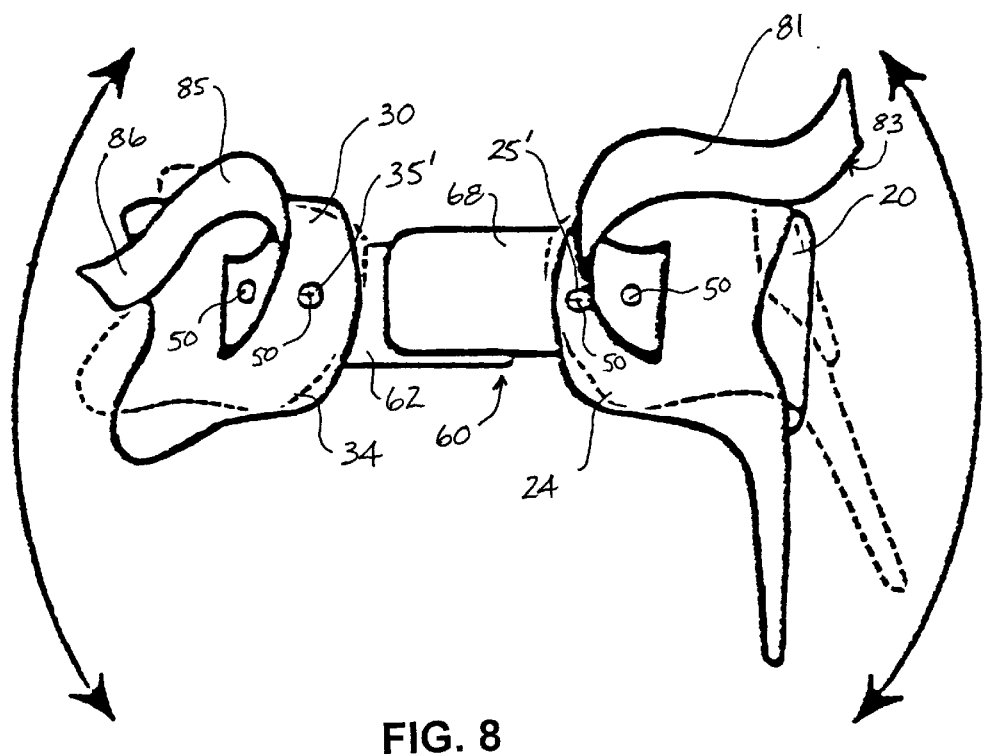
FIG. 8 is a front view of a rotationally adjustable anterior panel mounted to a first hip plate and a second hip plate of a pelvic bracing system, according to one preferred embodiment of this invention.

Referring to FIGS. 7 and 8, anterior panel 60 allows the adjustment of pelvic bracing system 15 laterally and/or rotationally with respect to a patient's anterior pelvic region. As shown in FIG. 7, anterior lateral adjustment is accomplished by adjusting the connection between inner plate 62 and outer plate 68.

Anterior rotational adjustment is accomplished by means similar to the rotational adjustment of posterior panel 40. As shown in FIG. 8, first hip plate 20 is rotationally adjustable with respect to outer plate 68 by guiding adjustment screw 50 along arcuate-shaped second plate adjustment slot 72. Adjustment screw 50 or a rivet positioned within second plate attachment aperture 70 acts as a pivot point for guiding adjustment screw 50 along second plate adjustment slot 72. Similarly, second hip plate 30 is rotationally adjustable with respect to inner plate 62 by guiding adjustment screw 50 along arcuate-shaped first plate adjustment slot 66, while adjustment screw 50 or a rivet positioned within first plate attachment aperture 64 acts as a pivot point for guiding adjustment screw 50 along first plate adjustment slot 66. First hip plate 20 and second hip plate 30 are rotationally adjusted until first hip plate 20 and second hip plate 30 are positioned properly with respect to the anterior pelvic region. Adjustment screws 50 are then tightened to secure first hip plate 20 and second hip plate 30 to anterior panel 60.

Figure 9:
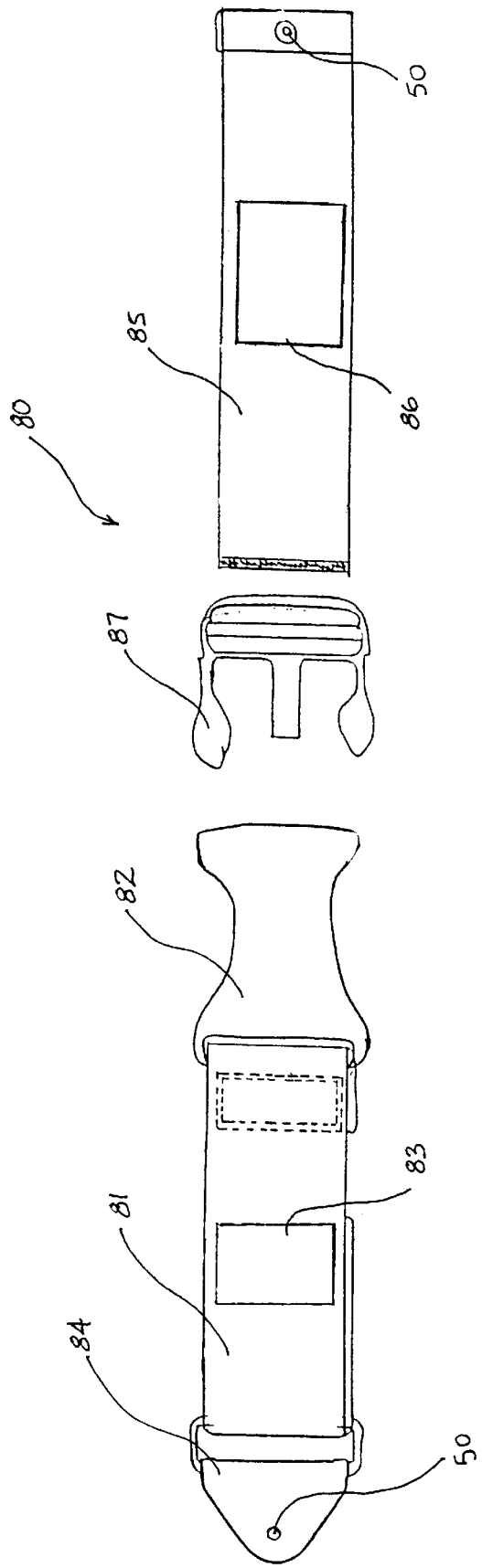
FIG. 9 is a front view of an adjustable belt of a pelvic bracing system, according to one preferred embodiment of this invention.

In one preferred embodiment of this invention, pelvic bracing system 15 further comprises a belt 80, as shown in FIG. 9. Preferably, as shown in FIGS. 7 and 8, belt 80 is positioned over anterior panel 60 to connect first hip plate 20 with respect to second hip plate 30. Preferably, but not necessarily, belt 80 comprises a removeable first strap 81 having a removeable female buckle portion 82. At least a portion of an outer surface 83 of first strap 81 comprises a fastening means, for example VELCRO brand hook and loop fastener or other fastening system known to those having ordinary skill in the art. Preferably, but not necessarily, first strap 81 is connected to a chaff and loop 84. Preferably, chaff and loop 84 is connected to first hip plate 20 at second plate attachment aperture 70 with adjustment screw 50 or other fastening means, for example a rivet.

Belt 80 further comprises a second strap 85, preferably connected to second hip plate 30 at first attachment aperture 64 with adjustment screw 50 or other suitable fastening means, for example a rivet or a chaff and loop 84 (not shown on second strap 85). At least a portion of an inner surface 86 of second strap 85 comprises a fastening means, for example VELCRO brand hook and loop fastener, compatible with the fastening means of outer surface 83 of first strap 81. Preferably, second strap 85 comprises a removeable male buckle portion 87 mateable with female buckle portion 82 to connect first hip plate 20 with second hip plate 30.

In one preferred embodiment of this invention, first strap 81 is disconnected from chaff and loop 84 and male buckle portion 87 is removed from second strap 85. Second strap 85 is insertable through chaff and loop 84 to connect first hip plate 20 with second hip plate 30. Preferably, at least a portion of an outer surface of second strap 85 comprises a fastening means, for example VELCRO brand hook and loop fastener, to secure second strap 85 to itself after second strap 85 is inserted through chaff and loop 84.

In one preferred embodiment of this invention, inner plate 62 and outer plate 68 are positioned so that an inner surface of inner plate 62 contacts an outer surface of outer plate 68. Thus, the fastening means of inner plate 62 does not contact the fastening means of outer plate 68. Belt 80 contacts the fastening means of inner plate 62 and is then utilized to fasten anterior portions 24 and 34 to one another.

In one preferred embodiment of this invention, a universal mounting block 95 is mounted with respect to first hip plate 20 and/or second hip plate 30. Preferably, but not necessarily, mounting block 95 is mounted to an extended portion 21 of first hip plate 20, as shown in FIG. 2. Extended portion 21 extends downwardly along a patient's leg to provide further support for pelvic bracing system 15 and to prevent uncomfortable contact between an articulating orthopedic joint (not shown in FIG. 2), mounted with respect to first hip plate 20, and the patient's leg. Mounting block 95 comprises a plurality of threaded channels 97 to accept corresponding articulating orthopedic joints. Threaded channels 97 are positioned to accept various orthopedic joints, which are attached to a thigh cuff (not shown in FIG. 2) to add support to pelvic bracing system 15.

While in the foregoing specification this invention has been described in relation to certain preferred embodiments thereof, and many details have been set forth for purpose of illustration, it will be apparent to those skilled in the art that the system and method according to this invention are susceptible to additional embodiments and that certain of the details described herein can be varied considerably without departing from the basic principles of the invention.

I claim:

1. A pelvic bracing system comprising:
   a first hip plate having a first attachment aperture and a first adjustment slot on a posterior portion of the first hip plate;
   a second hip plate having a second attachment aperture and a second adjustment slot on a posterior portion of the second hip plate;
   an anterior panel having a plurality of connecting apertures connected with respect to an anterior portion of the first hip plate and an anterior portion of the second hip plate with a plurality of adjustment screws; and
   a posterior panel having a sizing channel positioned at each end portion connected with respect to the posterior portion of the first hip plate and the posterior portion of the second hip plate with a plurality of adjustment screws.

2. The pelvic bracing system of claim 1 wherein at least one of the first adjustment slot and the second adjustment slot is configured in an arcuate shape.

3. The pelvic bracing system of claim 1 wherein the first hip plate and the second hip plate each is laterally adjustable with respect to the posterior panel.

4. The pelvic bracing system of claim 1 wherein the first hip plate and the second hip plate each is rotationally adjustable with respect to the posterior panel.

5. The pelvic bracing system of claim 1 wherein the first hip plate and the second hip plate each is laterally adjustable with respect to the anterior panel.

6. The pelvic bracing system of claim 1 wherein the first hip plate and the second hip plate each is rotationally adjustable with respect to the anterior panel.

7. The pelvic bracing system of claim 1 wherein the anterior panel comprises a pair of mateable plates.

8. The pelvic bracing system of claim 7 wherein each mateable plate further comprises a plate attachment aperture and a plate adjustment slot for attachment with respect to the anterior portion of the first hip plate and the anterior portion of the second hip plate.

9. The pelvic bracing system of claim 1 wherein the adjustment screws comprise an adjustment screw and a nut having a mating surface between about 0.5 inch and about 1.0 inch in diameter.

10. The pelvic bracing system of claim 1 further comprising a belt connecting the first hip plate with respect to the second hip plate, the belt positioned over the anterior panel.

11. The pelvic bracing system of claim 10 wherein the belt comprises a removable first strap having a removable female buckle portion and a second strap having a removable male buckle portion mateable with the female buckle portion.

12. The pelvic bracing system of claim 11 wherein the first strap and the second strap each has a fastening means for connecting the first hip plate with the second hip plate.

13. A pelvic bracing system comprising:
   a first hip plate and a second hip plate pivotally connected with respect to one another;
   a pair of mateable plates connecting an anterior portion of the first hip plate with an anterior portion of the second hip plate; and
   a belt further connecting the first hip plate and the second hip plate, the belt positioned over the pair of mateable plates.

14. The pelvic bracing system of claim 13 wherein the belt has at least one of a removable female buckle portion and a removable male buckle portion.

15. The pelvic bracing system of claim 13 further comprising a posterior panel connected to a posterior portion of the first hip plate and a posterior portion of the second hip plate.

16. The pelvic bracing system of claim 13 wherein the first hip plate and the second hip plate are adjustable at least one of laterally and rotationally with respect to the pelvic bracing system.

17. A pelvic bracing system comprising:
   an anterior panel having two mateable plates, each mateable plate having a plate attachment aperture and a plate adjustment slot, the plate adjustment slot extending along an arc;
   a posterior panel having a pair of sizing channels extending toward each end of the posterior panel; and
   a first hip plate connected to a second hip plate with the anterior panel and the posterior panel to form a pelvic brace.

18. The pelvic bracing system of claim 17 wherein at least one of the first hip plate and the second hip plate is rotationally adjustable with respect to the anterior panel by guiding an adjustment screw along at least one of the plate adjustment slots extending along an arc.

19. The pelvic bracing system of claim 17 wherein at least one of the first hip plate and the second hip plate is laterally adjustable with respect to the posterior panel by guiding an adjustment screw along at least one of the sizing channels.

20. The pelvic bracing system of claim 17 wherein the first hip plate further comprises a universal mounting block having a plurality of threaded channels to accept an orthopedic joint.

\* \* \* \* \*